US006403769B1

(12) United States Patent
Larochelle et al.

(10) Patent No.: US 6,403,769 B1
(45) Date of Patent: Jun. 11, 2002

(54) FUSION PROTEINS THAT INCLUDE ANTIBODY AND NONANTIBODY PORTIONS

(75) Inventors: William J. Larochelle, Gaithersburg, MD (US); Stuart A. Aaronson, Great Falls, VA (US); Olaf Dirsch, Bethesda, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 08/613,743

(22) Filed: Feb. 22, 1996

Related U.S. Application Data

(63) Continuation of application No. 08/189,552, filed on Feb. 1, 1994.

(51) Int. Cl.$^7$ ........................... C12P 21/08; C07K 16/00
(52) U.S. Cl. ............................... 530/387.3; 530/387.1; 530/388.24
(58) Field of Search ........................... 424/130.1, 141.1, 424/120.1, 145.1, 158.1; 435/327, 328, 330, 331, 334, 336; 436/512, 547, 548; 514/2; 530/387.1, 387.3, 357.7, 388.15, 388.24, 399

(56) References Cited

U.S. PATENT DOCUMENTS 5,116,964 A * 5/1992 Capon et al. ............... 536/23.4

FOREIGN PATENT DOCUMENTS

| CA | 2007336 | 7/1990 | ......... G01N/33/577 |
| EP | 0 315 062 | 10/1988 | ........... C12N/15/00 |
| EP | 0 325 224 | 7/1989 | |
| WO | WO 91/05856 | 5/1991 | ............ C12N/5/12 |
| WO | WO 92/08495 | 5/1992 | .......... A61K/47/48 |

OTHER PUBLICATIONS

Yayon et al, EMBO J. 11(5): 1585–1890, 1990 A. Combined V reg. Segment Confers Lig. Specificity . . . .*
La Rochelle et al, Science 248: 1541–1544 (6/22/90) "Molecular Localization of The Transforming: Secretary . . . ".*
Aaronson, "Growth Factors and Cancer", Science 254: 1146–1153 (Nov. 22, 1991).
Bennett et al, "Extracellular Domain–IgG Fusion, Proteins for Three Human Natriuretic . . . ", The Journal of Biological Chemistry, 266(34): 23060–23067 (1991).
Betsholtz et al., "cDNA sequence and chromosomal localization of human platelet–derived . . . ", Nature, 320: 695–699 (1986).
Capon et al., "Designing CD4 Immunoadhesins for AIDS therapy", Nature, 337: 525–531 (1989).
Finch et al., "Human KGF is FGF–Related with Properties of a Paracrine Effector . . . ", Science, 245: 752–755 (1989).

Gillies et al., "Targeting Human Cytotoxic T Lymphocytes To Kill Heterologous . . . ", The Journal of Immun. 146(3):1067–1071 (Feb. 1, 1991).
Jäckle et al., "Trafficking of the Epidermal Growth Factor Receptor and Transferin in Three. . . ", The Journal of Biol. Chem., 266(3): 1396–1402 (1991).
Landolfi et al., "A Chimeric IL–2/Ig Molecule Possesses The Functional Activity Of Both Proteins . . . ", The Journal of Immunology, 146(3): 915–919 (1991).
Mark et al., "Expression and Characterization of Hepatocye Growth Factor Receptor–IgG Fusion . . .", The Journal of Biological Chemistry, 267(36): 26166–26171 (1992).
Matsui et al., "Independent expression of human α or β platelet–derived growth factor receptor . . . ", Proc. Natl. Acad. Sci. USA, 86: 8314–8318 (1989).
Shin et al., "Expression and characterization of a antibody binding specificity joined to . . . ", Proc. Nat'l. Acad. Sci. USA, 87: 5322–5326 (1990).
Wright et al., "Genetically Engineered Antibodies: Progress and Prospects", Crit. Rev. in Immun., 12(3,4): 125–168 (1992).
Cheon et al., "High–affinity binding sites for related fibroblast growth factor ligands reside within different receptor immunoglobulin–like domains", Proc. Nat'l. Acad. Sci. USA 91: 989–993 (Feb. 1994).
Heidaran et al. "β PDGFR–IgG chimera demonstrates that human β PDGFR Ig–like domains 1 to 3 are sufficient for high affinity PDGF BB binding", The FASEB Journal 9: 140–145 (Jan. 1995).
Lyman et al., "Molecular Cloning of a Ligand for the flt3/flk–2 Tyrosine Kinase Receptor: A Proliferative Factor for Primitive Hematopoietic Cells," Cells 75: 1157–1167 (Dec. 17, 1993).

* cited by examiner

Primary Examiner—Anthony C. Caputa
Assistant Examiner—Gary B. Nickol
(74) Attorney, Agent, or Firm—Needle & Rosenberg, P.C.

(57) ABSTRACT

The high affinity which is characteristic of homodimers of IgG heavy chains is achieved, along with favorable secretion and flexibility/adaptability properties, in a fusion protein that has a nonantibody portion, comprised of an effector domain, joined to the aminoterminal end of an IgG-derived sequence consisting of a hinge:$CH_2$:$CH_3$ segment which lacks a $CH_1$ domain, with a heterologous signal peptide preferably provided upstream of the nonantibody portion. Chimeric molecules of this structure can be secreted readily in stable form by mammalian cells transfected with DNA encoding the molecule, and are amenable to rapid, efficient purification to homogeneity, for example, using protein A. These molecules are effective substitutes for monoclonal antibodies in contexts such as flow cytometry, immunohistochemistry, immunoprecipitation and ELISAs. A fusion protein as described also can be used in screening for agonists and antagonists to the cognate binding partner of the nonantibody portion of the fusion protein. Moreover, chimeric molecules in which the nonantibody portion contains a growth factor domain are internalized, essentially like the natural growth factor, in contrast to the situation that generally pertains with respect to antibodies which are directed to external receptor domains.

5 Claims, 4 Drawing Sheets

|                | Xho I |
|---|---|
| (SEQ ID NO:8) HFc | CTC GAG AGC AGC ACC AAG GTG GAC AAG AAA |
| (SEQ ID NO:10) | L   E   S   S   T   K   V   D   K  K→ |
| (SEQ ID NO:9) spHFc | ...GTT CTG GCC CTC GAG AGC AGC ACC AAG GTG GAC AAG AAA |
| (SEQ ID NO:11) | V L A L E S S T K V D K K→ |

FUSION PROTEINS THAT INCLUDE ANTIBODY AND NONANTIBODY PORTIONS

This application is a continuation, division, of application Ser. No. 08/189,552, filed Feb. 1, 1994.

BACKGROUND OF THE INVENTION

Immunoglobulin (Ig) molecules have been the focus of ongoing research because they react with a diverse range of antigens, possess different effector functions, and are important biologically. Of particular interest is the principal serum immunoglobulin in mammals, IgG, which is the major constituent of the secondary immunological response to most antigens.

Immunoglobulin G is a tetramer composed of two identical light (L) chains and two identical heavy (H) chains joined, respectively, by disulfide linkages. The L chains fold into two functional domains, while the H chains fold into four or five. Each domain consists of about 100 to 120 amino acid residues.

The H- and L-chain halfmers are covalently bonded by disulfide bonds in the H-chain "hinge" region, as shown in FIG. 1. The number of hinge disulfide bonds is variable and depends on the H chain isotype. The hinge region is flexible and susceptible to proteolytic digestion.

So-called "variable" regions, formed by the N-terminal domains for each chain, differ from antibody to antibody in amino acid sequence and define antigen-binding sites of unique specificity and affinity. The other IgG "constant" (C) domains, $CH_1$, $CH_2$ and $CH_3$, have the same amino acid sequence for a given antibody chain of the same isotype, except for single-residue differences at a few positions, and contribute to the activation of host effector mechanisms to eliminate antigen.

The V domains of the IgG molecule thus are responsible for antigen recognition and the binding of antigens, while the C domains mediate binding of the immunoglobulin to host cells, including various cells of the immune system and some phagocytic cells, and to $C_1q$, the first component of the classic complement system. More specifically, $C_1q$ interacts with the $CH_2$ domain of IgG. Among four recognized IgG subtypes, two (IgG1 and IgG3) possess higher complement fixation activity than the others (IgG2 and IgG4).

The domain structure of IgG and other antibodies recommend them as targets for protein engineering. See Rothwell, *Nature* 342: 99 (1989). Past efforts in this regard, as reviewed, for example, by Wright et al., *Crit. Rev. Immunol.* 12: 125 (1992), focussed on creating potentially valuable agents for treatment of human disease. Much of this "antibody engineering" involved maintaining the original specificity of the V region for a given Ig molecule while altering the remainder of the molecule, for example, by attaching an enzyme, toxin or growth factor to all or part of the molecule. See, for example, Shin & Morrison, *Proc. Nat'l Acad. Sci. USA* 87: 5322 (1990) (insulin-like growth factor 1 replaces constant region of mouse human IgG3 anti-dansyl antibody). Conversely, chimeric molecules were produced in which the V region was replaced with all or part of another molecule, including receptor molecules such as CD4 [Capon et al., *Nature*: 525 (1989)], human natriuretic peptide receptor [Bennett et al., *J. Biol. Chem.* 266: 23060 (1991)] and human hepatocyte growth factor receptor [Mark et al., *ibid.* 267: 26166 (1992)], and the cytokine interleukin-2 [Landolfi, *J. Immunol.* 146: 915 (1992)].

These IgG-containing fusion proteins demonstrated the feasibility of maintaining Ig effector function upon replacement of the variable region not only with a nonantibody component like CD4, which is associated with the so-called "immunoglobulin superfamily" and, hence, folds in a manner compatible with the IgG constant region, but also by a nonantibody domain like IL-2, which is structurally disparate to those of the Ig superfamily. For example, Landolfi (1992) took note of a "potential to create a variety of immunoligands in which the binding specificity is non-Ig in nature (e.g., hormone, lectin, peptide, or other ligand)," and he speculated that such "agents could have therapeutic potential if their binding specificity is unique to a neoplasia or other tissue characteristic of a disease state." Id. at 918.

Nevertheless, practical applications of such IgG-based chimeras actually has been slow to emerge. This is due in part to the fact that H and L chains of IgG are poorly secreted and rapidly degraded in the absence of partner L and H chains, respectively, a situation that applies to the chimeric molecules in question. There also is relatively little specific information or predictive theory to illuminate the biological properties of different categories of chimeric molecules.

SUMMARY OF THE INVENTION

It is therefore an object of the present invention to provide IgG/non-IgG fusion proteins which, upon heterologous expression in transfected mammalian cells, are potently secreted in stable form, and which display effector properties characteristic of antibody and nonantibody predecessor molecules, respectively.

It is another object of the present invention to provide an approach for producing Fc-containing chimeric molecules in a form that is readily useable in applications conventionally associated with monoclonal antibodies, including flow cytometry, immunohisto-chemistry and immunoprecipitation.

In accomplishing these and other objects, there has been provided, in accordance with one aspect of the present invention, a fusion protein comprising (A) an IgG sequence, (B) a nonantibody sequence covalently joined to the aminoterminal end of the IgG sequence and (C) a heterologous signal peptide that is covalently joined to the aminoterminal of the nonantibody sequence, wherein (i) the IgG sequence consists essentially of a hinge region, a $CH_2$ domain and a $CH_3$ domain, in that order, the IgG sequence lacking a $CH_1$ domain, (ii) the nonantibody sequence comprises an effector domain of a molecule, and (iii) the effector domain displays an activity that is characteristic of the effector domain in the molecule.

In accordance with another embodiment of the present invention, there has been provided a fusion protein comprising a nonantibody sequence covalently joined to the aminoterminal end of an IgG sequence that consists essentially of a hinge region, a $CH_2$ domain and a $CH_3$ domain, in that order, the IgG sequence lacking a $CH_1$ domain, wherein the nonantibody sequence comprises an effector domain of a growth factor molecule that in nature binds a single-unit receptor, such that the fusion protein induces DNA synthesis, as measured by uptake of $^3$H-thymidine, in a target cell.

In accordance with a further embodiment of the present invention, there has been provided a method for detecting a pathological condition associated with overexpression of a molecule that participates in a binding interaction, comprising the steps of (A) providing a fusion protein comprising a nonantibody sequence covalently joined to the aminoterminal end of an IgG sequence that consists essentially of a hinge region, a $CH_2$ domain and a $CH_3$ domain, in that order, the IgG sequence lacking a $CH_1$ domain, wherein the nonantibody sequence comprises an effector domain of a molecule, and wherein the effector domain displays an activity that is characteristic of the effector domain in the molecule;

(B) bringing the fusion protein into contact with a biological sample which contains a binding partner for the effector domain; and (C) monitoring binding of the effector domain by the binding partner in the sample to detect overexpression, relative to a control, of the binding partner.

In accordance with a further embodiment of the present invention, there has been provided a method for identifying agonists and antagonists that interfere with a binding interaction, comprising the steps of (A) providing a fusion protein comprising a nonantibody sequence covalently joined to the aminoterminal end of an IgG sequence that consists essentially of a hinge region, a $CH_2$ domain and a $CH_3$ domain, in that order, the IgG sequence lacking a $CH_1$ domain, wherein the nonantibody sequence comprises an effector domain of a molecule, and wherein the effector domain displays an activity that is characteristic of the effector domain in the molecule;

(B) in the presence of a putative agonist or antagonist to binding between the effector domain and a binding partner thereof, bringing the fusion protein into contact with a sample that contains the binding partner; and then (C) determining whether the putative agonist or antagonist did affect binding of the effector domain by the binding partner.

In accordance with another embodiment, there has been provided recombinant DNA molecules encoding fusion proteins of the present invention.

DETAILED DESCRIPTION OF PREFERRED EMBODIMENTS

It has been discovered that the high affinity which is characteristic of homodimers of IgG heavy chains is achieved, along with favorable secretion and flexibility/adaptability properties, in a fusion protein that has a nonantibody portion, comprised of an effector domain from a growth factor or growth factor receptor, joined to the aminoterminal end of an IgG-derived sequence consisting essentially of a hinge:$CH_2$:$CH_3$ segment which lacks a $CH_1$ domain. A sequence "consisting essentially of" this segment may include other components that do not materially affect the salient properties of the fusion protein, such as its ability to be secreted in stable form upon heterologous expression (see below). An example of an IgG-derived sequence is a $\gamma_1$ sequence consisting of a hinge region, a $CH_2$ domain and a $CH_3$ domain.

It also has been found that a heterologous signal peptide, provided upstream of the nonantibody portion of a chimeric molecule within the present invention, generally effects secretion of the fusion protein. This is true even when the nonantibody portion of the fusion protein is a intracellular protein or a segment of a molecule which is not secreted per se.

Chimeric molecules of the present invention are readily secreted in stable form by mammalian cells transfected with DNA that codes for the molecule. In addition, they are amenable to rapid, efficient purification to homogeneity, for example, using protein A. Because these molecules therefore are obtainable in a commercially useful amount and form, they are advantageous substitutes for monoclonal antibodies in contexts such as flow cytometry, immunohistochemistry, immunoprecipitation and enzyme-linked immunoadsorbant assays (ELISAs).

Also, a category of chimeric molecules according to the present invention is especially noteworthy for the mitogenic activity displayed by the fusion proteins within the category. In particular, it has been discovered that mitogenicity characterizes those fusion proteins of the present invention in which the nonantibody portion contains an effector domain of a growth factor that in nature binds a receptor that is a "single-unit" receptor, i.e., one that is not multi-unit receptor, such as the high-affinity IL-2 receptor, which is comprised of an α chain, β chain and a γ chain.

Figure 1:
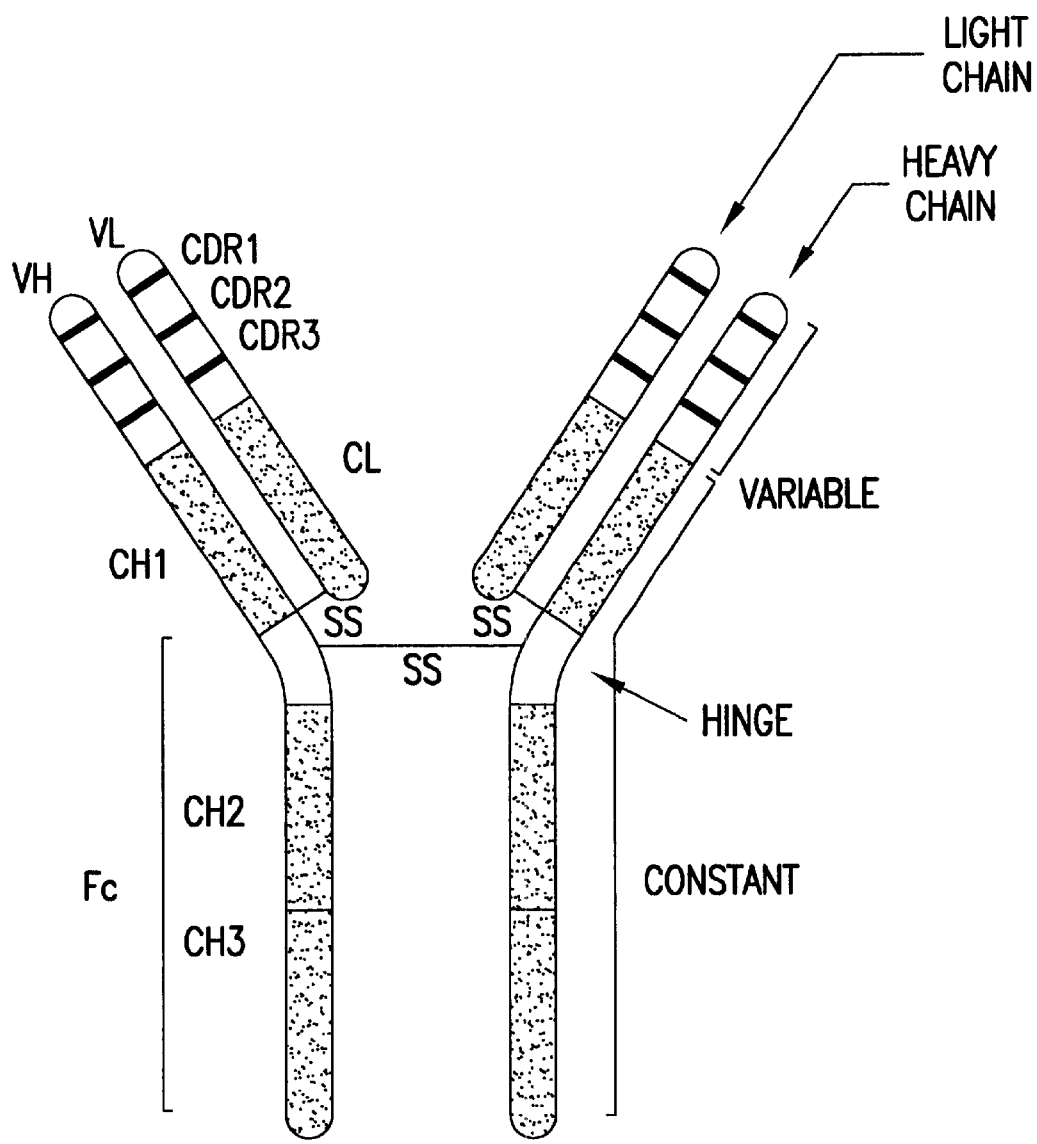
FIG. 1 presents a schematic depiction of the structure of the IgG antibody molecule. The V(L) and V(H) represent the light and heavy chain variable regions, respectively. The three complementarity-determining regions in the V(L) and V(H) domains are shown in heavier lines. The shaded areas are the constant regions of the L and H chains. The heavy chain consists of $CH_1$, $CH_2$ and $CH_3$ domains. The two heavy chains are connected by disulfide bonds (SS) in the hinge region.
Figure 2:
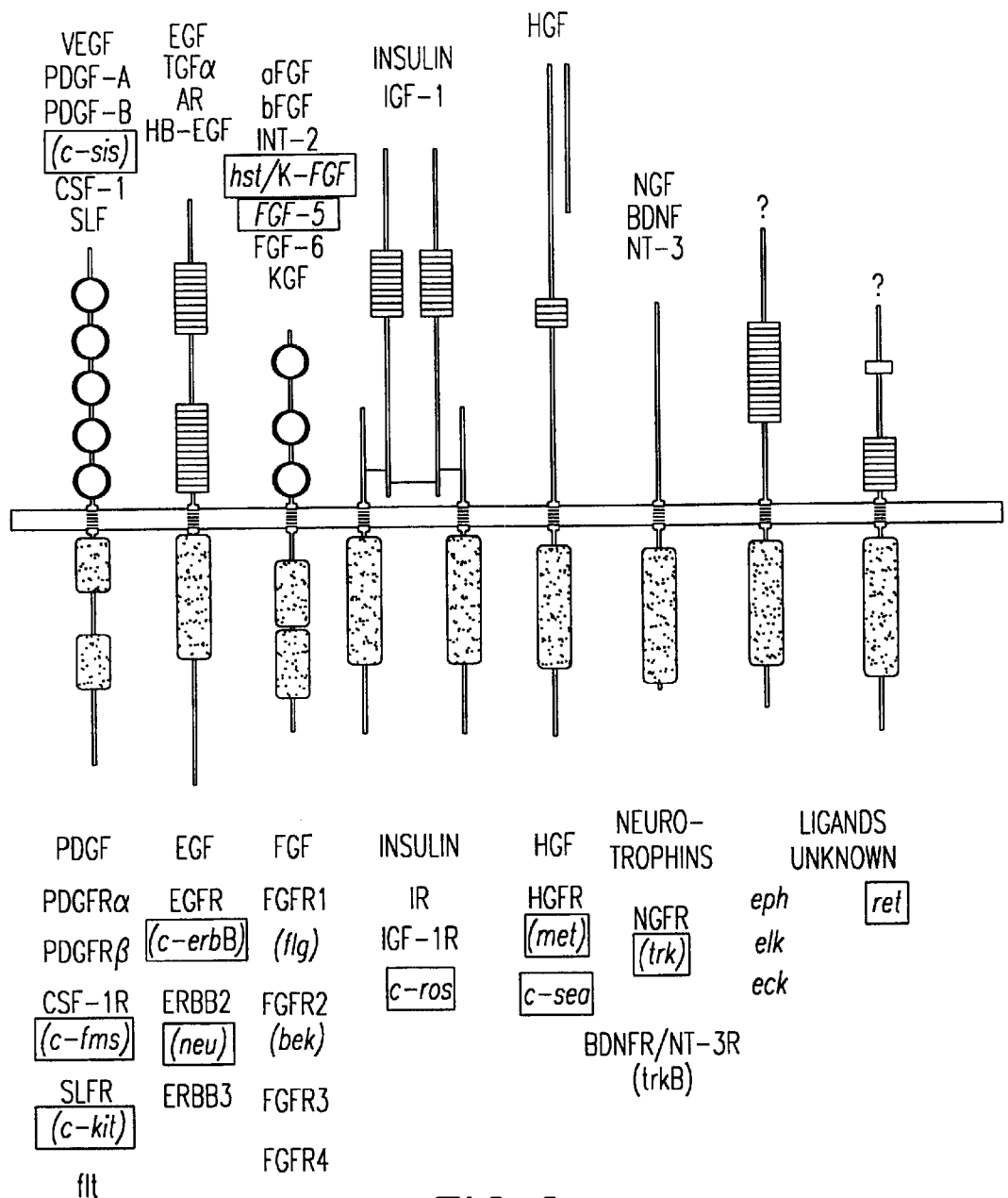
FIG. 2 is a line drawing displaying representative tyrosine-kinase receptors. Growth factors known to bind to receptors of a given family are listed above, and receptors that constitute each family are listed below. Boxes denote those growth factors or receptors the genes of which were identified initially as activated oncogenes. The c-onc designation is used to specify cellular homologs of retroviral oncogenes. Open circles illustrate Ig-like repeats. Dashed boxes indicate cysteine-rich domains. Dotted boxes indicate conserved tyrosine kinase domains.

Especially preferred in this regard are fusion proteins in which the nonantibody portion contains an effector domain of a growth factor that in nature binds a single-unit receptor having intrinsic tyrosine kinase activity. FIG. 2 illustrates that such receptors include an extracellular ligand-binding domain and an intracellular tyrosine-kinase domain responsible for transducing the mitogenic signal consequent upon binding of the cognate GF. See Aaronson, *Science* 254: 1146 (1991), the contents of which are hereby incorporated by reference.

Fusion proteins in the aforementioned category undergo internalization by receptor-mediated endocytosis, essentially like the natural GF, in contrast to the situation that typically pertains with antibodies directed to external receptor domains. In this context, "internalization" denotes movement of the fusion protein into a cell which carries the cognate receptor and then through intracellular compartments associated with receptor-ligand uncoupling and receptor recycling, respectively, to compartment(s) where the fusion protein accumulates and, ultimately, is degraded. See Jäckle et al., *J. Biol. Chem.* 266: 1396 (1991), the contents of which are hereby incorporated by reference. Thus, the fusion proteins in question are believed not to collect in an intracellular compartment associated with receptor recycling and, hence, are not subject to returning to the cell surface with recycled receptor. Consequently, these fusion proteins represent an especially effective means for delivering bioactive molecules and imaging agents to the interior of targeted cells.

The effect of such fusion protein internalization may be observed as an alteration in cellular growth and/or differentiation. For example, a keratinocyte growth factor fusion protein can induce a mitogenic response in BALB/MK cells, as shown in Example 2, below. It is expected that fusion proteins comprising a growth factor effector domain induce a change in cellular growth and/or differentiation via signal pathways essentially like natural growth factors.

A "growth factor" (GF) in the present description is a polypeptide that modulates the growth and/or metabolism of a target cell by binding to a receptor protein that is bound to the extracellular membrane of the target cell. Examples of GFs include platelet-derived growth factor (PDGF), keratinocyte growth factor (KGF), epidermal growth factor (EGF), vascular endothelial growth factor (VEGF), insulin, nerve growth factor (NGF), insulin-like growth factor (IGF), transforming growth factor (TGF), hepatic growth factor (HGF), fibroblast growth factor (FGF), the product of the Wnt-2 proto-oncogne (wnt-2). Aaronson, supra; Norman et al., HORMONES, pp. 719–748 (Academic Press 1987). Also, see generally, Heath (ed.), GROWTH FACTORS, IRL Press (1990).

A "growth factor receptor" (GFR) is a membrane-spanning protein that mediates the effects of a GF via an extracellular GF-binding domain. Illustrative GFRs are PDGFR, KGFR, EGFR, HGFR, FGFR1, insulin receptor, IGF-1R, HGFR ("Met") and NGFR. Preferred GFRs have at least one domain comprising two B-sheets that form a sandwich which is stabilized by a disulfide bond. Such a structure is referred to as an "immunoglobulin (Ig)-like domain."

An "effector domain" of a molecule is a portion of the molecule that is responsible for a functional characteristic of that molecule. For example, the effector domain of a GF is a portion of a GF that binds to the cognate receptor, while the effector domain of a GFR refers to a portion of a GFR that binds with the cognate ligand. Accordingly, an "activity that is characteristic" of a GF effector domain and a GFR effector domain includes binding to a cognate GFR and a cognate GF, respectively. In this description, the phrase "nonantibody sequence" denotes an amino acid sequence for one or more effector domains of a molecule that is not an antibody.

A "signal peptide" is an amino acid sequence that facilitates the passage of a secreted protein molecule or a membrane protein molecule across the endoplasmic reticulum. Kreil, *Ann. Rev. Biochem.* 50: 317 (1981); Walter et al., *Cell* 38:5 (1984). In eukaryotic cells, signal peptides share the characteristics of (1) an N-terminal location on the protein; (2) a length of about 16 to about 35 amino acid residues; (3) a net positively charged region within the first 2 to 10 residues; (4) a central core region of at least 9 neutral or hydrophobic residues capable of forming an alpha-helix; (5) a turn-inducing amino acid residue next to the hydrophobic core; and (6) a specific cleavage site for a signal peptidase. von Heijne, *Nucl. Acids Res.* 14: 4683 (1986). Numerous specific signal peptides have been documented and can be found, for example, in Table 21-7 of Darnell et al., MOLECULAR CELL BIOLOGY (Scientific American Books, Inc. 1986).

In the present context, a "heterologous" signal peptide is one not associated in nature with the nonantibody portion of a fusion protein within the resent invention. Suitable heterologous signal peptides nclude signal peptides that are associated in nature ith a GF or GFR, such as a protein selected from the roup consisting of PDGF A, PDGF B, KGF, vascular endothelial growth factor (VEGF), KGF receptor (KGFR) and β PDGF receptor (β PDGFR).

An "intracellular protein" in this description is a protein, such as p53 protein, retinoblastoma (Rb) protein and ras, that normally is not secreted by a cell which synthesizes it and that contains effector domains such as those involved in protein interactions, nucleic acid interactions or enzymatic functions.

A "marker moiety" in the present description refers to molecule that will generate a signal under predetermined conditions. Examples of marker moieties include radioisotopes, enzymes, fluorescent labels, chemiluminescent labels, bioluminescent labels and paramagnetic labels.

I. PRODUCTION OF FUSION PROTEINS

A. Construction of Fusion Protein Expression Vectors

To produce a fusion proteins which comprises antibody and nonantibody portions and which is secreted in stable form by mammalian cells, according to the present invention, DNA sequences coding for the fusion protein are subcloned into an expression vector which is used to transfect mammalian cells. General techniques for producing fusion proteins comprising antibody sequences are described in Coligan et al. (eds.), CURRENT PROTOCOLS IN IMMUNOLOGY, at pp. 10.19.1–10.19.11 (Wiley Interscience 1992), the contents of which are hereby incorporated by reference. See also METHODS: A COMPANION TO METHODS IN ENZYMOLOGY, Volume 2 (No. 2), Academic Press (1991), and ANTIBODY ENGINEERING: A PRACTICAL GUIDE, W. H. Freeman and Company (1992), in which commentary relevant to production of fusion proteins is dispersed throughout the respective texts.

Thus, the first step in the construction of fusion proteins is to subclone portions of the fusion proteins in cloning vectors. In this context, a "cloning vector" is a DNA molecule, such as a plasmid, cosmid or bacteriophage, that can replicate autonomously in a host prokaryotic cell. Cloning vectors typically contain one or a small number of restriction endonuclease recognition sites at which foreign DNA sequences can be inserted in a determinable fashion without loss of an essential biological function of the vector, as well as a marker gene-that is suitable for use in the identification and selection of cells transformed with the cloning vector. Marker genes typically include genes that provide tetracycline resistance or ampicillin resistance. Suitable cloning vectors are described by Sambrook et al. (eds.), MOLECULAR CLONING: A LABORATORY MANUAL, Second Edition (Cold Spring Harbor Press 1989) (hereafter "Sambrook"); by Ausubel et al. (eds.), CURRENT PROTOCOLS IN MOLECULAR BIOLOGY (Wiley Interscience 1987) (hereafter "Ausubel"); and by Brown (ed.), MOLECULAR BIOLOGY LABFAX (Academic Press 1991). Cloning vectors can be obtained, for example, from GIBCO/BRL (Gaithersburg, Md.), Clontech Laboratories, Inc. (Palo Alto, Calif.), Promega Corporation (Madison, Wis.), Stratagene Cloning Systems (La Jolla, Calif.), Invitrogen (San Diego, Calif.), and the American Type Culture Collection (Rockville, Md.).

The DNA sequence encoding the Ig portion of a fusion protein within the present invention preferably encodes an Ig heavy chain. More preferably, such a DNA sequence encodes the hinge, CH2 and $CH_3$ domains of IgG, as indicated above. Immunoglobulin DNA sequences can be obtained using the polymerase chain reaction (PCR) as described, for example, by Coligan et al. (eds.), CURRENT PROTOCOLS IN IMMUNOLOGY, pages 10.20.1–10.20.8 (Wiley Interscience 1992) (hereafter "Coligan").

By one approach, antibody DNA sequences are amplified from RNA of cells that synthesize an immunoglobulin. Larrick et al., "PCR Amplification of Antibody Genes," in 2 METHODS: A COMPANION TO METHODS IN ENZYMOLOGY 106 (1991). Briefly, total RNA is isolated from immunoglobulin-producing cells using standard techniques. See Ausubel at pages 4.1.2–4.2.8. Poly A+ RNA then is isolated from total RNA using the standard technique of oligo-dT column chromatography as described, for instance, by Sambrook Single-stranded cDNA molecules then are synthesized from poly A+ RNA using reverse transcriptase. Techniques for synthesizing CDNA are described in each of Sambrook, Ausubel, and Coligan. Moreover, commercially available kits can be used to synthesize cDNA molecules. For example, such kits are available from GIBCO/BRL (Gaithersburg, Md.), Clontech Laboratories, Inc. (Palo Alto, Calif.), Promega Corporation (Madison, Wis.) and Stratagene Cloning Systems (La Jolla, Calif.).

The PCR reaction is performed with the single-stranded cDNA template and a mixture of oligonucleotide primers. The design of oligonucleotide primers can be based upon the DNA sequence of the immunoglobulin of interest. Alternatively, oligonucleotide primers can be designed based on information from a database of immunoglobulin amino sequences, such as Kabat et al., SEQUENCES OF PROTEINS OF IMMUNOLOGICAL INTEREST, U.S. Department of Health and Human Services (1983), taking into account degeneracies for each amino acid. Oligonucleotide synthesis and purification techniques are described in Sambrook and Ausubel, respectively. The PCR procedure is performed via well-known methodology. See, for example, Ausubel, Coligan, and Bangham, "The Polymerase Chain Reaction: Getting Started," in PROTOCOLS IN HUMAN MOLECULAR GENETICS (Humana Press 1991). Moreover, PCR kits can be purchased from companies such as Stratagene Cloning Systems (La Jolla, Calif.) and Invitrogen (San Diego, Calif.).

Alternatively, immunoglobulin-encoding DNA sequences can be synthesized using PCR with cloned immunoglobulins. This approach is illustrated below in Example 1.

DNA sequences encoding GF or GFR effector domains can be synthesized using PCR with RNA isolated from cells that produce the GF or GFR proteins, as described above. Preferably, GFR DNA sequences encode one or more effector domains having the structure of Ig-like domains.

Alternatively, DNA sequences encoding GF or GFR effector domains can be obtained using PCR with a GF cDNA or GFR cDNA template, as illustrated below in Example 1. In addition, GF- and GFR-encoding clones are available commercially from the American Type Culture Collection (ATCC; Rockville, Maryland USA), among other sources. See, for example, ATCC accession Nos. 57346 and 57415 (EGF receptor clones) and ATCC accession No. 41033 (PDGF B clone).

DNA sequences that encode heterologous signal peptides can be obtained via PCR with RNA isolated from cells that produce GF or GFR proteins, as described above. Such DNA sequences also can be obtained by isolating fragments of GF or GFR cDNAs that encode a signal peptide. For example, the PDGF A signal peptide used in the expression vector construct of Example 1 was obtained from the 5'-end of a PDGF A cDNA clone described by Betsholtz et al., Nature 320: 695 (1986), the contents of which are hereby incorporated by reference.

Alternatively, DNA sequences encoding signal peptides can be obtained by synthesizing oligonucleotides that encode known signal peptide amino acid sequences.

Such amino acid sequences are disclosed, for example, by Darnell et al., supra, and Wallis et al., THE BIOCHEMISTRY OF THE POLYPEPTIDE HORMONES, page 212 (John Wiley & Sons 1985). Techniques for oligonucleotide synthesis are disclosed, for example, by Ausubel at pp. 2.11.1–2.12.5. Also, see generally Eckstein et al. (ed.), OLIGONUCLEOTIDES AND ANALOGUES: A PRACTICAL APPROACH (IRL Press 1992).

DNA sequences encoding a heterologous signal peptide are subcloned in frame with DNA sequences encoding the N-terminus of a GF or GFR effector domain, while DNA sequences encoding the GF or GFR effector domain are subcloned in frame with the N-terminus of the antibody portion of the fusion protein. Subcloning is performed in accordance with conventional techniques, such as the use of restriction enzyme digestion to provide appropriate termini, the use of alkaline phosphatase treatment to avoid undesirable joining of DNA molecules, and ligation with appropriate ligases. Techniques for such manipulation are described by Sambrook and Ausubel, and are well-known in the art. Techniques for amplification of cloned DNA in bacterial hosts and isolation of cloned DNA from bacterial hosts also are well-known. Id.

The cloned fusion protein is cleaved from the cloning vector and inserted into an expression vector. Suitable expression vectors typically contain (1) prokaryotic DNA elements coding for a bacterial replication origin and an antibiotic resistance marker to provide for the growth and selection of the expression vector in a bacterial host; (2) eukaryotic DNA elements that control initiation of transcription, such as a promoter; and (3) DNA elements that control the processing of transcripts, such as a transcription termination/polyadenylation sequence.

A fusion protein of the present invention preferably is expressed in eukaryotic cells, such as mammalian, insect and yeast cells. Mammalian cells are especially preferred eukaryotic hosts because mammalian cells provide suitable post-translational modifications such as glycosylation. Examples of mammalian host cells include Chinese hamster ovary cells (CHO-K1; ATCC CCL61), rat pituitary cells (GH₁; ATCC CCL82), HeLa S3 cells (ATCC CCL2.2), rat hepatoma cells (H-4-II-E; ATCC CRL1548) SV40-transformed monkey kidney cells (COS-1; ATCC CRL 1650) and murine embryonic cells (NIH-3T3; ATCC CRL 1658). Preferably, the mammalian host cells are NIH-3T3 cells.

For a mammalian host, the transcriptional and translational regulatory signals may be derived from viral sources, such as adenovirus, bovine papilloma virus, simian virus, or the like, in which the regulatory signals are associated with a particular gene which has a high level of expression. Suitable transcriptional and translational regulatory sequences also can be obtained from mammalian genes, such as actin, collagen, myosin, and metallothionein genes.

Transcriptional regulatory sequences include a promoter region sufficient to direct the initiation of RNA synthesis. Suitable eukaryotic promoters include the promoter of the mouse metallothionein I gene (Hamer et al., *J. Molec. Appl. Genet.* 1: 273 (1982)]; the TK promoter of Herpes virus [McKnight, Cell 31: 355 (1982)]; the SV40 early promoter [Benoist et al., Nature 290: 304 (1981)]; the Rous sarcoma virus promoter [Gorman et al., *Proc. Nat'l Acad. Sci.* USA 79: 6777 (1982); and the cytomegalovirus promoter [Foecking et al., *Gene* 45: 101 (1980)].

Alternatively, a prokaryotic promoter, such as the bacteriophage T3 RNA polymerase promoter, can be used to control fusion gene expression if the prokaryotic promoter is regulated by a eukaryotic promoter. Zhou et al., *Mol. Cell. Biol.* 10: 4529 (1990); Kaufman et al., *Nucl. Acids Res.* 19: 4485 (1991).

An expression vector can be introduced into host cells using a variety of techniques including calcium phosphate transfection, liposome-mediated transfection, electroporation, and the like. Preferably, transfected cells are selected and propagated wherein the expression vector is stably integrated in the host cell genome to produce stable transformants. Techniques for introducing vectors into eukaryotic cells and techniques for selecting stable transformants using a dominant selectable marker are described by Sambrook, by Ausubel, by Bebbington, "Expression of Antibody Genes in Nonlymphoid Mammalian Cells," in 2 METHODS: A COMPANION TO METHODS IN ENZYMOLOGY 136 (1991), and by Murray (ed.), GENE TRANSFER AND EXPRESSION PROTOCOLS (Humana Press 1991).

Stable transformants that produce a fusion protein can be identified using a variety of methods. For example, stable transformants can be screened using an antibody that binds either to the nonantibody portion of the fusion protein or to the antibody portion of the fusion protein. The use of immunoprecipitation to identify cells that produce fusion proteins is illustrated in Example 2, below.

After fusion protein-producing cells have been identified, the cells are cultured and fusion proteins are isolated from culture supernatants. As described, for example, by Coligan, isolation techniques include affinity chromatography with Protein-A Sepharose, size-exclusion chromatography and ion exchange chromatography. Protein A preferably is used to isolate fusion proteins from supernatants.

B. Assay for Retained Effector Activity

Routine binding assays can be performed to determine whether the nonantibody portion of the fusion protein retains the ability to bind with its cognate ligand or receptor. For example, fusion proteins comprising a GFR domain can be tested using a competition binding assay, such as Scatchard analysis. Scatchard, *Ann. N.Y. Acad Sci.* 51: 660 (1949). In this example, Scatchard analysis is performed by measuring the binding of radiolabeled GF with the fusion protein comprising at least one cognate GFR effector domain in the presence of excess unlabeled GF. Conversely, fusion proteins containing a GF domain can be tested by measuring the binding of radiolabeled GF with a GFR membrane preparation, or with cells containing GFR, in the presence of excess unlabeled fusion protein. A binding test is illustrated below in Example 2.

Alternatively, the binding activity of a fusion protein comprising a GFR domain can be tested by measuring the ability of the fusion protein to inhibit a biological activity mediated by the cognate ligand of the GFR. In this type of assay, the fusion protein competes with the GFR of the target cell for a limited quantity of the cognate GF. Example 1 illustrates a mitoqenic assay in which a fusion protein comprising a GFR effector domain is used to inhibit a GF-mediated increase in DNA synthesis.

Conversely, fusion proteins comprising a GF effector domain can be tested by measuring the ability of the fusion protein to induce mitogenesis or transformation, as illustrated in Examples 2, 4, and 5.

II. USE OF FUSION PROTEINS FOR DIAGNOSIS AND THERAPY

A. Use of Fusion Proteins for Diagnosis

The presence of a particular GF or GFR can be detected in a biological sample using an in vitro assay. Accordingly, a fusion protein comprising a GF effector domain can be used to detect the presence of GFR in a biological sample, while a fusion protein comprising a GFR effector domain can be used to detect the presence of GF in a biological sample. In such in vitro assays, the fusion proteins may be used in liquid phase. For example, the presence of a GF in a biological sample can be tested by mixing the biological sample with a trace amount of labeled GF and a fusion protein comprising a GFR effector domain under conditions that promote the binding of GF to the fusion protein. Complexes of GF and fusion protein in the sample can be separated from the reaction mixture by contacting the complex with an immobilized protein which is specific for the antibody portion of the fusion protein, such as an Fc antibody or Staphylococcus protein A. The concentration of GF in the biological sample will be inversely proportional to the amount of labeled GF bound to the fusion protein and directly related to the amount of free labeled GF.

Alternatively, in vitro assays can be performed in which the fusion protein is bound to a solid-phase carrier. For example, fusion protein can be attached to a polymer, such as aminodextran, in order to link the antibody component of the fusion protein to an insoluble support such as a polymer-coated bead, a plate or a tube.

Other suitable in vitro assays will be readily apparent to those of skill in the art.

Fusion proteins of the present invention also can be used to detect the presence of particular proteins in tissue sections prepared from a histological specimen. Such in situ detection can be accomplished by applying a detectably-labeled fusion protein to the tissue sections. In situ detection can be used to determine the presence of a particular protein and to determine the distribution of the protein in the examined tissue. General techniques of in situ detection are well-known to those of ordinary skill. See, for example, Ponder, "Cell Marking Techniques and Their Application," in MAMMALIAN DEVELOPMENT: A PRACTICAL APPROACH 113–38 Monk (ed.) (IRL Press 1987), and Coligan.

Fusion proteins can be detectably labeled with any appropriate marker moiety, for example, a radioisotope, an enzyme, a fluorescent label, a chemiluminescent label, a bioluminescent labels or a paramagnetic label. Methods of making and detecting such detectably-labeled fusion proteins are well-known to those of ordinary skill in the art, and are described in more detail below.

The marker moiety can be a radioisotope that is detected by such means as the use of a gamma counter or a scintillation counter or by autoradiography. Isotopes that are particularly useful for the purpose of the present invention are $^{3}$H, $^{125}$I, $^{131}$I, $^{35}$S, $^{14}$C, and preferably $^{125}$I.

Fusion proteins also can be labeled with a fluorescent compound. The presence of a fluorescently-labeled fusion protein is determined by exposing the fusion protein to light of the proper wavelength and detecting the resultant fluorescence. Fluorescent labeling compounds include fluorescein isothiocyanate, rhodamine, phycoerytherin, phycocyanin, allophycocyanin, o-phthal-dehyde and fluorescamine. Fluorescently-labeled fusion proteins are particularly useful for flow cytometry analysis and immunohistochemical analysis, as illustrated in Example 2.

Alternatively, fusion proteins can be detectably labeled by coupling the fusion protein to a chemiluminescent compound. The presence of the chemiluminescenttagged fusion protein is determined by detecting the presence of luminescence that arises during the course of a chemical reaction. Examples of chemiluminescent labeling compounds include luminol, isoluminol, an aromatic acridinium ester, an imidazole, an acridinium salt and an oxalate ester.

Similarly, a bioluminescent compound can be used to label fusion proteins of the present invention. Bioluminescence is a type of chemiluminescence found in biological systems in which a catalytic protein increases the efficiency of the chemiluminescent reaction. The presence of a bioluminescent protein is determined by detecting the presence of luminescence. Bioluminescent compounds that are useful for labeling include luciferin, luciferase and aequorin.

Alternatively, fusion proteins can be detectably labeled by linking the fusion protein to an enzyme. When the fusion protein-enzyme conjugate is incubated in the presence of the appropriate substrate, the enzyme moiety reacts with the substrate to produce a chemical moiety which can be detected, for example, by spectrophotometric, fluorometric or visual means. Examples of enzymes that can be used to detectably label fusion proteins include malate dehydrogenase, staphylococcal nuclease, delta-V-steroid isomerase, yeast alcohol dehydrogenase, α-glycerophosphate dehydrogenase, triose phosphate isomerase, horseradish peroxidase, alkaline phosphatase, asparaginase, glucose oxidase, β-galactosidase, ribonuclease, urease, catalase, glucose-VI-phosphate dehydrogenase, glucoamylase and acetylcholinesterase.

Those of skill in the art will know of other suitable labels which can be employed in accordance with the present invention. The binding of marker moieties to fusion proteins can be accomplished using standard techniques known to the art. Typical methodology in this regard is described by Kennedy et al., *Clin. Chim. Acta* 70: 1 (1976), Schurs et al., *Clin. Chim. Acta* 81: 1 (1977), Shih et al., *Int'l J. Cancer* 46: 1101 (1990), and Coligan.

The above-described in vitro and in situ detection methods may be used to assist in the diagnosis or staging of a pathological condition. For example, such methods can be used to detect tumors that overexpress a particular GFR such as epidermal growth factor (EGF) receptor [Libermann et al., *Nature* 313: 144 (1985); Yamamoto et al., *Cancer Res.* 46: 141 (1986)], PDGFR [Fleming et al., *ibid.* 52: 4550 (1992); *Oncogene* 7: 1355 (1992)], and Met [Vande Woude, *Jap. J. Cancer Res.* 83 (1992)].

The present invention also contemplates the use of fusion proteins for in vivo diagnosis. The method of diagnostic imaging with radiolabeled proteins is well-known. In the technique of immunoscintigraphy, for example, antibodies are labeled with a gamma-emitting radioisotope and introduced into a patient. A gamma camera is used to detect the location and distribution of gamma-emitting radioisotopes. See, for example, Srivastava (ed.), RADIOLABELED MONOCLONAL ANTIBODIES FOR IMAGING AND THERAPY (Plenum Press 1988), Chase, "Medical Applications of Radioisotopes," in REMINGTON'S PHARMACEUTICAL SCIENCES, 18th Edition, Gennaro et al. (eds.), pp. 624–652 (Mack Publishing Co., 1990), and Brown, "Clinical Use of Monoclonal Antibodies," in BIOTECHNOLOGY AND PHARMACY 227–49, Pezzuto et al. (eds.) (Chapman & Hall 1993).

For diagnostic imaging, radioisotopes may be bound to the antibody portion of a fusion protein either directly, or indirectly by using an intermediary functional group. Useful intermediary functional groups include chelators such as ethylenediaminetetraacetic acid and diethylenetriaminepentaacetic acid. For example, see Shih et al., supra, and U.S. Pat. No. 5,057,313.

The radiation dose delivered to the patient is maintained at as low a level as possible through the choice of isotope for the best combination of minimum half-life, minimum retention in the body, and minimum quantity of isotope which will permit detection and accurate measurement. Examples of radioisotopes that can be bound to fusion protein and are appropriate for diagnostic imaging include $^{99m}$Tc and $^{111}$In.

Fusion proteins also can be labeled with paramagnetic ions for purposes of in vivo diagnosis. Elements that are particularly useful for magnetic resonance imaging include Gd, Mn, Dy and Fe ions.

B. Use of Fusion Proteins for Therapy

The approach to fusion protein therapy is similar to the approach used in monoclonal antibody therapy. In both situations, the objective is to deliver cytotoxic doses of radioactivity, toxin, or drug to target cells, while minimizing exposure to non-target tissues. Fusion proteins comprising a GF effector domain are preferred. Such fusion proteins will bind to target cells that express the cognate GFR in the extracellular membrane. In contrast to the situation that typically pertains with antibodies directed to external receptor domains, however, fusion proteins comprising a GF effector domain are internalized after binding to the cognate GFR, essentially like the natural GF.

Fusion proteins comprising GF effector domains can be used to treat, for example, tumors that overexpress GFR, such as glioblastomas and breast cancer.

As discussed above, a radioisotope can be attached to a fusion protein directly or indirectly, via a chelating agent. For example, $^{67}$Cu, considered one of the more promising radioisotopes for radioimmunotherapy due to its 61.5 hour half-life and abundant supply of beta particles and gamma rays, can be conjugated to a fusion protein using the chelating agent, p-bromoacetamidobenzyl-tetraethylaminetetraacetic acid (TETA). Chase, supra. Alternatively, $^{90}$Y, which emits an energetic beta particle, can be coupled to a fusion protein using diethylenetriaminepentaacetic acid (DTPA).

Alternatively, boron addends such as carboranes can be attached to fusion proteins. Carboranes can be prepared with carboxyl functions on pendant side chains, as is well-known in the art. Attachment of carboranes to a carrier, such as aminodextran, can be achieved by activation of the carboxyl groups of the carboranes and condensation with amines on the carrier. The intermediate conjugate is then conjugated to the fusion protein. After administration of the fusion protein conjugate, a boron addend is activated by thermal neutron irradiation and converted to radioactive atoms which decay by α-emission to produce highly toxic, short-range effects.

In addition, therapeutically useful fusion proteins can be prepared in which a fusion protein is conjugated to a toxin or drug. Illustrative of toxins which are suitably employed in the preparation of such conjugates are ricin, abrin, pokeweed antiviral protein, gelonin, diphtherin toxin, and Pseudomonas endotoxin. Useful chemotherapeutic drugs for the preparation of fusion protein conjugates include doxorubicin, daunorubicin, methotrexate, melphalin, chlorambucil, vinca alkaloids, 5-fluorouridine and mitomycin-C.

Since fusion proteins of the present invention which comprise GF effector domains are internalized, their efficacy when conjugated to a toxin or a drug generally will be greater that of corresponding antibody conjugates. Accordingly, a lower dose of the fusion protein conjugate may be administered to a patient, compared with the dose required for the corresponding antibody conjugate.

In general, the dosage of administered fusion protein conjugates will vary depending upon such factors as the patient's age, weight, height, sex, general medical condition and previous medical history. Typically, it is desirable to provide the recipient with a dosage of fusion protein conjugate which is in the range of from about 1 pg/kg to 10 mg/kg (amount of agent/body weight of patient), although a lower or higher dosage also may be administered as circumstances dictate.

Administration of fusion protein conjugates to a patient can be intravenous, intraarterial, intraperitoneal, intramuscular, subcutaneous, intrapleural, intrathecal, by perfusion through a regional catheter, or by direct intralesional injection. When administering fusion protein conjugates by injection, the administration may be by continuous infusion or by single or multiple boluses.

Fusion protein conjugates having a boron addend-loaded carrier for thermal neutron activation therapy will normally be effected in similar ways. However, it will be advantageous to wait until non-targeted fusion protein conjugate clears before neutron irradiation is performed. Clearance can be accelerated using an antibody that binds to the antibody moiety of the fusion protein. See U.S. Pat. No. 4,624,846 for a description of this general principle.

The fusion protein conjugates of the present invention can be formulated according to known methods to prepare pharmaceutically useful compositions, whereby fusion protein conjugates are combined in a mixture with a pharmaceutically acceptable carrier. A composition is said to be a "pharmaceutically acceptable carrier" if its administration can be tolerated by a recipient patient. Sterile phosphate-buffered saline is one example of a pharmaceutically acceptable carrier. Other suitable carriers are well-known to those in the art. See, for example, REMINGTON'S PHARMACEUTICAL SCIENCES, 18th Ed. (1990).

For purposes of therapy, a fusion protein conjugate and a pharmaceutically acceptable carrier are administered to a patient in a therapeutically effective amount. A combination of a fusion protein conjugate and a pharmaceutically acceptable carrier is said to be administered in a "therapeutically effective amount" if the amount administered is physiologically significant. An agent is physiologically significant if its presence results in a detectable change in the physiology of a recipient patient.

Additional pharmaceutical methods may be employed to control the duration of action of a fusion protein conjugate in a therapeutic application. Control release preparations can be prepared through the use of polymers to complex or adsorb the fusion protein conjugate. For example, biocompatible polymers include matrices of poly(ethylene-co-vinyl acetate) and matrices of a polyanhydride copolymer of a stearic acid dimer and sebacic acid. Sherwood et al., *Bio/Technology* 10: 1446 (1992). The rate of release of a fusion protein conjugate from such a matrix depends upon the molecular weight of the fusion protein conjugate, the amount of fusion protein conjugate within the matrix, and the size of dispersed particles. Saltzman et al., *Biophys. J.* 55: 163 (1989); Sherwood et al., supra. Other solid dosage forms are described in REMINGTON'S PHARMACEUTICAL SCIENCES, 18th ed. (1990).

III. WORKING EXAMPLES

Thus generally described, the present invention will be understood more readily by reference to the following examples, which are provided by way of illustration and are not intended to be limiting of the present invention.

EXAMPLE 1

Production and Analysis of Fusion Proteins comprising KGFR Effector Domains

A plasmid cloning vector pUC 18 which contained the immunoglobulin heavy chain gene hinge, $CH_2$ and $CH_3$ domains was constructed and designated "HFc-pUC 18." To engineer this construct, the HFc portion of the sis 1 immunoglobulin heavy chain cDNA was amplified by PCR utilizing primer sequences:

5' (680-) CGTCTGGATCCCTCGAGAGCAGCAC-CAAGGTGGACAAGAAA (SEQ ID NO: 1) and

3' (1390-) TCTCCGGATCCCTGGGATCATTTACCAG-GAGAGTG (SEQ ID NO:2). The polymerase chain reaction kit and thermocycler were obtained from Perkin-Elmer Co. (Norwalk, CT), and PCR was performed according to the manufacturer's protocol. The Ig heavy chain-encoding CDNA was obtained from a cDNA library prepared from a hybridoma which produced an anti-PDGF monoclonal antibody, sis 1, as described in U.S. application Ser. No. 07/365,715 (filed Jun. 14, 1989), the contents of which are hereby incorporated by reference.

The HFc PCR product contained a XhoI cloning site in frame with the HFc cDNA and BamHI excision sites at the 5' and 3' ends. A second plasmid cloning vector, designated spHFc-pUC 18, was also engineered containing a PDGF A signal peptide, as a "generic signal peptide," in frame with the XhoI cloning site and the HFc CDNA.

PCR also was used to amplify keratinocyte growth factor receptor (KGFR) cDNA corresponding to Ig-like effector domains D2 and D3 (nucleotides 650 to 1450), D2 alone (nucleotides 650 to 1130), or D3 alone (nucleotides 1132 to 1359). Miki et al., *Science* 251: 72–75 (1991). Primer sequences used for PCR were as follows:

5' (650-) TTAAGGTCGACAGAGGACCAGGGATTG-GCACTGTG (SEQ ID NO:3);

3' (1450-) ATAGCGTCGACGGAAGCCGTGATCTC-CTTCTCTCT (SEQ ID NO:4);

3' (1130-) ATAGCGTCGACGGAGGCATTTGCAG-GCAGTCCAGC (SEQ ID NO:5);

5' (1132-) TTAAGGTCGACACGGTGGTCGGAGGG-GATGTGGAG (SEQ ID NO:6);

3′ (1359-) ATAGCGTCGACGGAGACCTTA-CATATATTCCCCAGC (SEQ ID NO:7).

Figure 3:
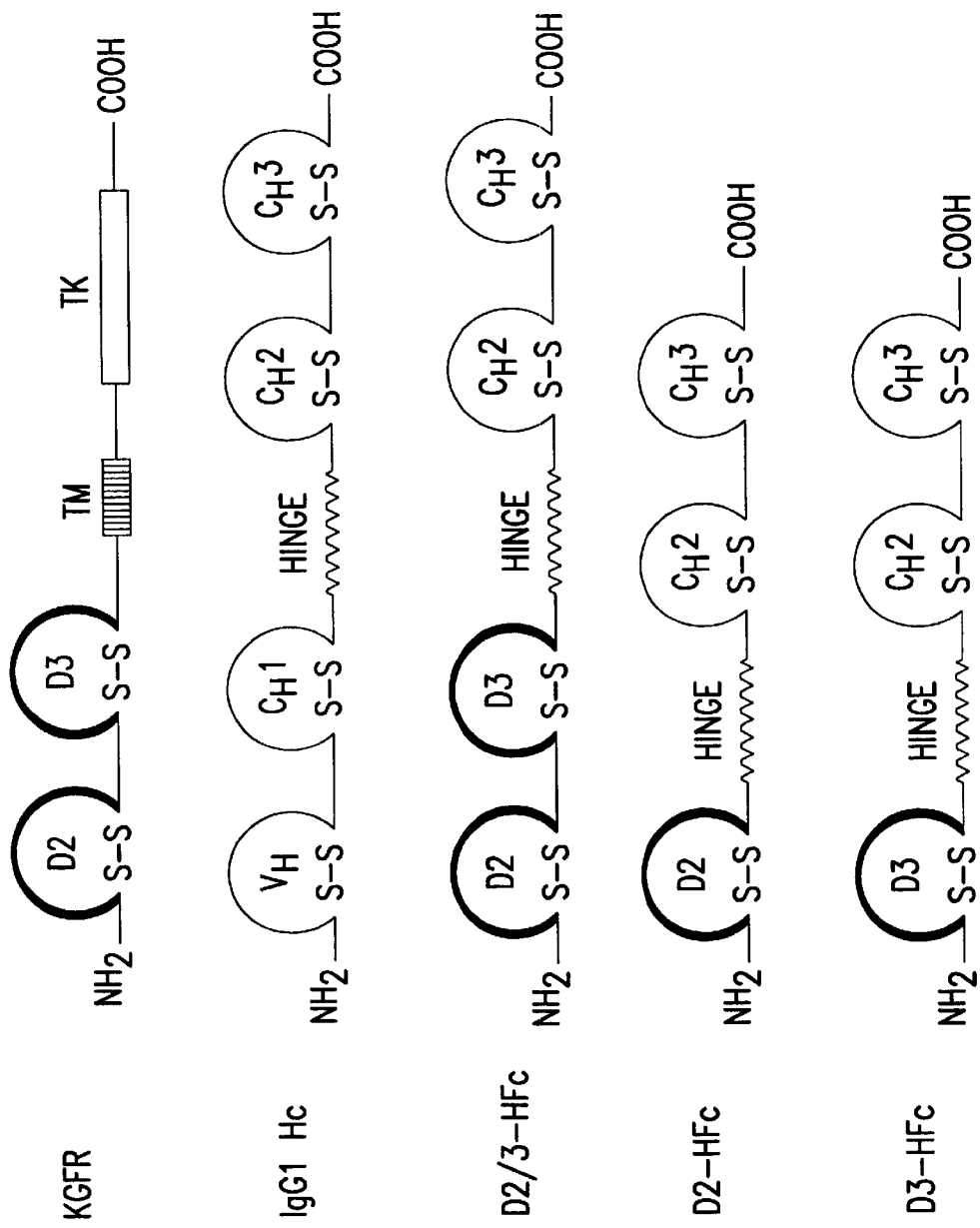
FIG. 3 is a schematic representation of molecules, including certain fusion proteins within the present invention, that pertain to Example 1, below.

D2/3 and D2 extracellular domain PCR products were then cloned into the HFc-pUC 18 construct in frame with HFc CDNA using XhoI compatible ends generated by PCR. The D3 domain was cloned into spHFc-pUC18. KGFR-HFC constructs are diagrammed in FIG. 3.

Restriction endonuclease digestion using BamHI excised each KGFR-HFc chimeric cDNA from pUC 18 vectors. KGFR DNA fragments were then cloned into the BglII site of the mouse metallothionine vector, MMTneo. The MMTneo expression vector contained an ampicillin resistance gene which selects for growth in bacterial cells, as well as a neomycin gene which allows mammalian cell growth in the presence of geneticin, "G418."

Plasmid DNAs from D2/3-HFc, D2-HFc and D3-HFc MMTneo constructs were introduced into NIH 3T3 cells with 40 µg of carrier calf thymus DNA by the calcium phosphate precipitation technique. Wigler et al., Cell 11: 223 (1977). Established transfectants were cultured in the presence of G418 containing medium.

Cells were incubated in the presence of radiolabeled amino acids to examine the expression of the fusion proteins. Briefly, cell cultures were washed and incubated for 30 min in methionine- and cysteine-free Dulbecco's modified Eagle minimal essential medium (DMEM) containing 25 µM zinc chloride, as described by LaRochelle et al., J. Biol. Chem. 267: 17074 (1992), followed by metabolic labeling with [$^{35}$S]-methionine (125 µCi/ml) and [$^{35}$S]-cysteine (125 µCi/ml) for 3 hr. Conditioned medium was collected and immunoprecipitated with S. aureus protein A Sepharose CL-4B (Pharmacia LKB Biotechnology; Piscataway, N.J.) which recognized the Fc portion of the chimeric gene products. The immunoprecipitated proteins were then analyzed by SDS-polyacrylamide gel electrophoresis (PAGE) and immunoprecipitated species were visualized after fluorography.

The results of these studies showed that the D2/3-HFc fusion protein migrated as a predicted 80 kd species by SDS-PAGE performed under reducing conditions, while the D2-HFc and D3-HFc fusion proteins each resolved at 55 kd. As a control, conditioned media from NIH 3T3 cells showed no corresponding radiolabeled protein A immunoreactive species. Under nonreducing conditions, D2/3-HFc, D2-HFc, and D3-HFc migrated at 160, 110, and 110 kd, respectively. Thus, like the IgG molecule having an HFc portion that covalently dimerizes, each KGFR-HFc gene product was secreted as a disulfide-linked dimer that retained protein A binding determinants.

An in vitro binding assay was developed to determine whether the KGFR-HFc fusion proteins possessed binding determinants of the native KGFR. To study the binding characteristics of the fusion proteins, KGFR-HFcs (20 µg) were partially purified by protein A column chromatography as previously described. Ey et al., Immunochem. 15: 429 (1978). For Scatchard analysis, each KGFR-HFc was incubated at 4° C. in 200 µl of RIP buffer (10 mM Tris, 0.25 M NaCl, 1 mM EDTA, 10 mM KCl, 1% NP-40, 0.1% SDS, 0.05% Tween 20)/0.3% milk with varying concentrations of either radioiodinated KGF (270,000 cpm/ng) or a radioiodinated bovine fibroblast growth factor (aFGF) (29,000 cpm/ng) in the absence or presence of a hundred-fold excess of unlabeled ligand. Recombinant human KGF was purified and labeled with $^{125}$I as described by Bottaro et al., J. Biol. Chem. 265: 12767 (1990). Bovine brain aFGF was obtained from Upstate Biotechnology, Inc. (Lake Placid, N.Y.). $^{125}$I-aFGF was prepared as described by Friesel et al., J. Biol. Chem. 261: 7581 (1986).

After 5 hr incubation, 30 µl of a 50% solution of Gamma Bind G, which had been previously blocked with 3.0% milk/PBS and re-equilibrated in PBS, was added to the incubation mixture, shaken vigorously for 1 hr, pelleted, and washed three times with the buffer (0.5 ml each). Bound ligand recovered from the pellets was counted in a Beckman gamma counter. Specific binding was defined as the difference between binding in the absence or presence of excess unlabeled ligand.

Saturable binding was achieved between 15 ng/ml and 25 ng/ml of KGF, and between 40 ng/ml and 50 ng/ml of aFGF. The dissociation constant for each fusion protein was determined by measuring the concentrations of unlabeled ligand required for 50% displacement of radiolabeled ligand. When KGF was used as the ligand, the dissociation constants for the D2/3-HFc, D2-HFc and D3-HFc4 fusion proteins were determined to be 120 pM, greater than 2.0 µM, and 20 pM, respectively. The dissociation constant for the D2/3-HFc fusion protein was very similar to that of native KGFR expressed by epithelial cells (180 pM).

When aFGF was used as the ligand, the D2/3-HFc fusion protein exhibited saturable aFGF binding activity with an apparent dissociation constant of 520 pM, which is similar to that of the native KGFR (600 pM). In marked contrast to the results obtained with KGF, the D2-HFc fusion protein bound aFGF with high affinity (960 pM), while the D3-HFc fusion protein failed to detectably interact with aFGF under the same conditions (dissociation constant>2.0 µM). The results of the binding studies indicate that the third Ig-like domain of the KGFR contained the major KGF binding site while the second Ig-like domain contained the major determinants responsible for high affinity aFGF interactions.

The results of the binding studies suggested that the KGFR D2 and D3-HFc fusion proteins might act as specific antagonists of KGF or aFGF, respectively. To test this possibility, quiescent Balb/MK cells, which express the native KGFR, were exposed to different ligands and [$^3$H]-thymidine uptake measured in the presence of increasing concentrations of each KGFR-HFC chimera. Thymidine incorporation into Balb/MK mouse epidermal keratinocytes was performed as described by Rubin et al., Proc. Nat'l Acad. Sci. USA 86: 802 (1989). The Balb/MK cell line is described in Weissman et al., Cell 32: 599 (1983). Briefly, varying concentrations of each KGFR-HFc protein were added to quiescent Balb/MK cells followed by the addition of the appropriate ligand. Ligand concentrations were used that produced an approximately eighty percent induction of maximal DNA synthesis. Cells were incubated at 37° C. for 16 hr and [$^3$H]-thymidine added for the final 5 hr. Cells were washed, harvested, and [$^3$H]-thymidine uptake was measured by liquid scintillation counting.

The results of these studies showed that the D2/3-HFc fusion protein inhibited KGF and aFGF-induced DNA synthesis to similar extents with detectable effects observed at a concentration of 2 mg D2/3-HFc fusion protein/ml. However, even at concentrations as high as 100 mg/ml, the same fusion protein showed no detectable effect on the thymidine incorporation in response to either bFGF or the unrelated epidermal growth factor (EGF) molecule. As further specificity controls, neither a nonspecific IgG (MOPC21) nor conditioned medium from NIH 3T3 cells detectably inhibited [$^3$H] thymidine uptake in response to any of the ligands.

The pattern of inhibition observed with the D2-HFc fusion protein was consistent with its high affinity and specific binding of aFGF. The D2-HFc fusion protein inhibited aFGF mitogenic activity but had no effect on KGF, bFGF, or EGF. In contrast, the D3-HFc fusion protein specifically blocked KGF-induced thymidine uptake, but had no detectable effects on aFGF, bFGF or EGF. Thus, the D2-HFc fusion protein acted as a selective antagonist of aFGF, while D3-HFc uniquely blocked KGF mitogenic actions.

EXAMPLE 2

Production and Analysis of Fusion Proteins Comprising KGF Effector Domains

Figure 4:
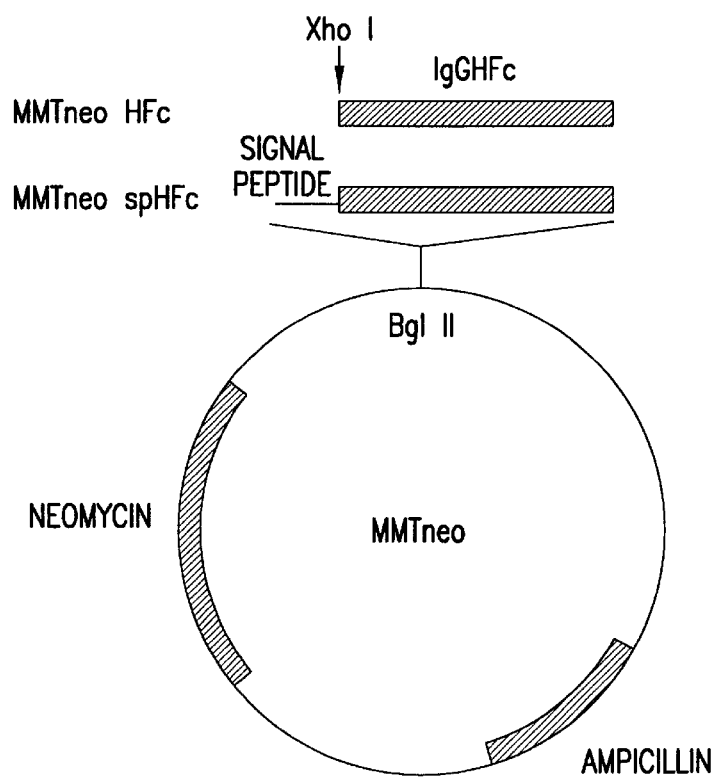
FIG. 4 diagrammatically depicts the construction of a plasmid (MMTneo), as described below in Example 2, which contains DNA coding for a KGF-HFc fusion protein within the present invention. The Fc portion of the immu- noglobulin heavy chain gene was cloned in the BamHI sight of pUC 18 after PCR was used to generate BamHI-compatible ends. Two constructs were engineered, respectively, with and without a heterologous signal peptide, as shown in panel A. Panel A also shows the adjoining cDNA sequence, as well as the encoded amino acids. The BamHI cloning sites of HFc-pUC 18 or spHFc-pUC 18 ultimately facilitated cloning in the Bgl II site of the MMTneo expression vector, resulting in the vectors MMTneo-HFc or MMTneo-spHFc (panel B). The latter vector was generated by adding the PDGF A signal peptide upstream and in frame with the Xho I cloning site of MMTneo-HFc (Panel A). The HFc or spHFc PCR products also contained an Xho I cloning site which was introduced by PCR, 5' and in frame with the HFc region but following the 5' BamHI site. Thus, GF or GFR cDNAs were amplified by PCR with either Xho I- or Sal I-compatible ends, were restriction enzyme-digested, and then were ligated into the MMTneo HFc vector in frame with the IgG HFc domain.

In order to develop high affinity probes of growth factor receptors with the detection properties of an immunoglobulin, a fusion protein was designed in which KGF cDNA, see Finch et al., Science 245: 752 (1989), was recombined with the HFc portion of mouse IgG heavy-chain cDNA at the hinge region, as shown in FIG. 4. In accordance with Example 1 above, the HFc portion consisted of the immunoglobulin heavy chain hinge, $CH_2$ and $CH_3$ domains.

Expression vectors were constructed using techniques described in Example 1. Briefly, PCR was used to generate BamHI compatible ends on the HFc portion of the immunoglobulin heavy chain gene. The HFc fragment was then cloned into the BamHI site of pUC 18. The HFc cDNA insert was also engineered by PCR to contain an XhoI cloning site in frame and 5' to the HFc region, but within the BamHI sites, shown in FIG. 4. The HFc fragment, which contained BamHI compatible ends, was removed by restriction digestion and cloned into the BglII site of the MMTneo vector.

KGF cDNA was amplified by PCR with either XhoI or SalI compatible ends, digested with restriction enzyme, and subcloned into the MMTneo HFc vector in frame with the IgG HFc domain. The resultant expression vector is designated "KGF-HFc MMTneo."

NIH 3T3 cells were transfected with KGF-HFc MMTneo and stable transformants were selected using G418, as described in Example 1.

To determine whether the KGF-HFc fusion protein was expressed by transfected cells and possessed structural determinants of both KGF and the immunoglobulin HFc domain, cell cultures were incubated with $^{35}$S-methionine and $^{35}$s-cysteine, as described in Example 1. Although protein A Sepharose CL-4B could be used to detect the presence of fusion protein in conditioned media, recovery was increased by approximately fifteen- to twenty-fold when conditioned media were first treated with either KGF monoclonal antibody or anti-mouse Fc antibody to precipitate fusion protein. Isolated proteins were analyzed using SDS-PAGE.

In one set of experiments, conditioned media were treated with a KGF monoclonal antibody, followed by immunoprecipitation with protein A Sepharose. SDS-PAGE showed three distinct p94–98 immunoreactive species. In a second set of experiments, conditioned media were treated with anti-mouse IgG Fc, before treatment with protein A Sepharose. Again, p94–98 species were observed. In contrast, these species were not found in immunoprecipitates of conditioned medium from control MMTneo transfectants.

Since the KGF-HFc fusion protein possessed the hinge region of IgG heavy chain, which is known to dimerize, studies were performed to determine whether the KGF-HFc fusion protein was a disulfide linked dimer. Addition of 100 mM dithiothreitol to the KGF-HFc gene product reduced the migration of the KGF monoclonal antibody or anti-mouse HFc immunoreactive species to an apparent molecular weight of 48 kd. These results indicate that the KGF-HFc fusion protein possesses the structural determinants of both KGF and the immunoglobulin Fc domain. Furthermore, the KGFR-HFc dimerizes biochemically like the parental immunoglobulin.

To determine whether the KGF-HFC fusion protein possessed the biologic properties of the KGF, the ability of the fusion protein to induce $^3$H-thymidine uptake in BALB/MK cells was examined, using the assay described in Example 1. The results of these studies showed that 85 pM KGFR-HFc fusion protein stimulated $^3$H-thymidine uptake at least twenty-fold. Comparison to recombinant KGF demonstrated that the KGF-HFc fusion protein half-maximally stimulated $^3$H-thymidine uptake at around 45 pM, while recombinant KGF half-maximally stimulated $^3$H-thymidine uptake at around 10 pM. Control conditioned medium showed little mitogenic activity. In addition, a KGF neutralizing monoclonal antibody inhibited the mitogenic activity of the fusion protein by greater than seventy-five percent. Moreover, heparin in the range of 1 to 5 µg/ml also inhibited the mitogenic activity of KGF-HFc and a mitogenically equivalent amount of KGF by greater than eighty percent.

The ability of the KGF-HFc fusion protein to bind to its cognate receptor was tested using 32D cells transfectants that expressed the KGFR. In brief, 32D cells were harvested by centrifugation, washed in DMEM, gently resuspended in binding buffer (DMEM/25 mM HEPES pH 7.4 with 1 mg/ml bovine serum albumin), and maintained at 37° C. Next, saturating levels of radioiodinated KGF (2 ng) were added with increasing concentrations of unlabeled KGF-HFc fusion protein competitor, partially purified by protein A chromatography, in 50 µl of binding buffer at 4° C. About 1.2×10⁶32D cells were added in an equivalent volume of binding buffer and incubated at 16° C. After one hour, the cell suspension was layered onto 300 µl of a chilled oil mix (n-butyl phthalate (Fischer)/Bis (2-ethylhexyl) phthalate (Kodak) 1.5:1). Cells were centrifuged in an Eppendorf microfuge at 10,000 rpm for 10 minutes at 4° C. The cell pellet was removed and counted in a Beckman 5500 gamma counter.

The results of these studies showed that the KGF-HFc fusion protein bound to the 32D-KGFR with an affinity of about 1.4 nM, while recombinant KGF bound to the 32D-KGFR with an affinity of about 0.13 nM. Typically, recombinant KGF possesses a five- to ten-fold higher binding affinity for the KGFR than KGF expressed by mammalian systems.

Accordingly, these results indicate that the KGF-HFc fusion protein possesses the functional mitogenic and binding properties of KGF.

Members of the fibroblast growth factor receptor (FGFR) superfamily, such as bek and fig, bind aFGF and bFGF, but do not bind KGF. In order to examine the specificity of the KGF-HFc fusion protein, the fusion protein was incubated with B5-589 cells, or with NIH 3T3 cells transfected with either KGFR, bek, or flg. Bound primary antibody was detected with rabbit anti-mouse IgG conjugated with fluorescein isothiocyanate. As a control, the fusion protein was incubated with untransfected NIH 3T3 cells. Flow cytometric analysis was performed using a fluorescent-activated cell sorter (FACSCAN analyzer).

The results of flow cytometry analysis showed that KGFR-containing B5-589 and NIH 3T3 transfectants were recognized by the KGF-HFC fusion protein as indicated by a 10 to 100-fold increase in fluorescent intensity, compared to untransfected NIH 3T3 cells. But NIH 3T3 cells containing the alternative spliced FGFR isoforms bek and flg did not show an increased staining over the background of untransfected NIH 3T3 cells. As a further control, the HFc portion of IgG also failed to recognize the KGFR-containing B5-589 or NIH 3T3 transfectants. Therefore, the KGF-HFc immunochemical recognition was specific for the presence of the KGFR and failed to recognize at least two other closely-related members of the FGFR superfamily.

Similar flow cytometry studies demonstrated that wnt-2-FHc and β PDGF-HFc fusion proteins bound to the wnt-2 receptor and β PDGFR, respectively.

Immunohistochemistry was performed using frozen sections of human skin. Conditioned medium from KGF-HFc transfectants was purified or used directly for detection of KGFR. Bound KGF-HFc was detected with rabbit anti-mouse horseradish peroxidase using standard protocols. The results are summarized in Table 1. The intensity of KGF-HFc staining varied from no detectable staining ("−") to high intensity staining ("+++"). As a control, KGF was found to compete with KGF-HFc fusion protein and decrease staining by labeled fusion protein. Control immunoglobulin HFc showed no staining.

TABLE 1

Detection of KGFR with KGFR-HFc

| Tissue | Intensity of Staining |
| --- | --- |
| Spiral Artery | +++ |
| Endothelium of Uterus | |
| No Treatment | +++ |
| Estrogen | +++ |
| Estrogen + Progesterone | + |
| Endometrium of Placenta | − |
| Normal Skin | |
| Stratum Basale | − |
| Stratum Spinosum | +++ |
| Stratum Granulosum | + |
| Hair Follicle (bulb) | +++ |
| Sweat Glands | − |
| Schwann Cells | + |
| Psoriatic Epithelium | − |
| Wound Healing Epithelium | − |
| Days 1–10 | |
| Day 10+ | +++ |
| Irritated Skin | − |
| +Retinoic Acid Treatment | +++ |
| Stomach | |
| Surface Epithelium | + |
| Mesenchyme | − |
| Prostate | |
| Epithelium | ++ |
| Tumor Cell Lines | |
| SMU16 | +++ |
| MDA-11B 453 | + |
| MDA-11B 458 | − |

In analogous studies, the KGFR-HFC fusion protein was used to detect the presence of KGF in normal human skin. The presence of KGF was detected in the stratum basale. In contrast, KGF was not detected in either the stratum spinosum or stratum granulosum. Control immunoglobulin HFc showed no staining.

EXAMPLE 3

Production and Analysis of Fusion Proteins Comprising PDGFR Effector Domains

In order to develop an efficacious screening method for the identification of β B PDGFR antagonists, a fusion protein was constructed comprising β PDGFR domains 1 through 3 (D1-3) and the HFc domain. Matsui et al., *Proc. Nat'l Acad. Sci. USA* 86: 8314-18 (1989). The β PDGFR-HFC fusion protein was constructed via techniques essentially as described in Example 1.

NIH 3T3 cells were transfected and the β PDGFR-HFc fusion protein was analyzed, as described above. The β PDGFR-HFc fusion protein was expressed by transfected cells as a 200 kd dimeric molecule and was recognized by anti-mouse Fc antibody. Scatchard analysis showed that the β PDGFR-HFc fusion protein had an affinity for PDGF BB of about 1.5 nM.

To screen for β PDGFR antagonists, an assay was developed which is similar to a standard enzyme-linked immunosorbant assay (ELISA). Briefly, 10 ng of PDGF BB were immobilized to the wells of a Falcon 3912 flexible assay plate in phosphate-buffered saline containing 0.2% sodium azide (PBS-SA). Wells were blocked for 30 minutes with PBS-SA containing 4% bovine serum albumin. β PDGFR-HFc fusion protein was added to the wells in PBS-SA containing 1% bovine serum albumin (BSA) and 0.05% Tween 20, the plates were incubated for 4 hours at room temperature, and wells were washed with PBS-SA containing 0.05% Tween 20. Rabbit anti-mouse Fc, which had been conjugated with alkaline phosphatase, was added to the wells in PBS-SA containing 1% BSA and 0.05% Tween 20 at a concentration of 5 μg antibody per milliliter buffer solution. After a two hour incubation, wells were washed, and alkaline phosphatase substrate was added to the wells in 100 mM sodium bicarbonate (pH 9.8)-1 mM magnesium chloride. After another incubation, the presence of the product of the chromogenic substrate was measured at 405 nm using an ELISA reader.

The screening assay demonstrated that the β PDGFR-HFc fusion protein, but not HFc or MOPC 21, bound to the PDGF BB protein. Binding of the β PDGFR-HFC fusion protein to PDGF BB was comparable to the binding expected for a high affinity PDGF BB monoclonal antibody. In contrast, the β PDGFR-HFc fusion protein did not bind to PDGF AA under incubation conditions in which PDGF AA was bound by an anti-PDGF AA monoclonal antibody. Thus, the screening assay can be used to identify agonists and antagonists of a GFR.

EXAMPLE 4

Production and Analysis of Fusion Proteins Comprising PDGF Effector Domains

To develop probes of growth factor receptors, fusion proteins were constructed comprising the HFc region and effector domains of PDGF A, PDGF B or KGF, as described above. The fusion proteins were constructed using techniques essentially as described in Example 1.

Transfection of NIH 3T3 cells and analysis of fusion proteins were performed as described above. PDGF A-HFc fusion protein and PDGF B-HFc fusion protein were expressed by transfected cells as 84–89 kd and 84 kd dimeric proteins, respectively. Both fusion proteins were recognized by anti-PDGF antibody and by anti-mouse Fc antibody, respectively.

Scatchard analysis showed that the PDGF A-HFC fusion protein bound the α PDGFR with an affinity of 1.3 nM, but did not bind with the β PDGFR. In contrast, the PDGF B-HFc fusion protein bound with both α PDGFR and β PDGFR with affinities of 3.2 nM and 1.4 nM, respectively.

Both PDGF A-HFC fusion protein and PDGF B-HFC fusion protein stimulated $^3$H-thymidine uptake in NIH 3T3 cells in the concentration range of 50 to 600 pM.

Also, both fusion proteins were used to immunoprecipate PDGFRs by incubating fusion proteins with PDGFR, treating the PDGFR-fusion protein complexes with anti-mouse Fc, and incubating the ternary complexes with protein A Sepharose CL-4B.

EXAMPLE 5

Construction and Transforming Activity of PDGF A-HFC Fusion Proteins

PDGF A-HFc fusion proteins were constructed by using PCR to amplify PDGF A cDNA between codons 1 and 144 (A[1-144]HFc), between codons 1 and 80 (A[1-80]HFc), or between codons 95 and 177 (A[95-177]HFc) with either XhoI- or SalI-compatible ends. PDGF A DNA sequences were ligated into the XhoI site of the MMTneo HFc vector in frame with the mouse immunoglobulin IgG1 heavy chain HFc domain.

For analysis of transforming activity, plasmid DNA from each recombinant was introduced into NIH 3T3 cells by transfection with the recombinant plasmid DNA and 40 μg of carrier calf thymus DNA using the calcium phosphate technique. Transfected cultures were scored for colony formation in the presence of G148 or focus formation two to three weeks after transfection. Colony formation following selection in medium containing G148 was used as an internal marker of transfection efficiency. As a negative control, 0.1 μg of the mouse metallothionein vector was transfected.

The results of these studies showed that fusion proteins PDGF A[-180]HFc and PDGF A[95-177]HFc have the ability to transform NIH 3T3 cells, while fusion protein PDGF A[1-144]HFc lacked this ability. Therefore, codons 95-177 correspond to the minimal PDGF A transforming domain. The fusion proteins PDGF A[1-80]HFc and PDGF A[95-177]HFc had nearly identical transforming activity, in comparison with PDGF A.

SEQUENCE LISTING

<160> NUMBER OF SEQ ID NOS: 11

<210> SEQ ID NO 1
<211> LENGTH: 41
<212> TYPE: DNA
<213> ORGANISM: Artificial Sequence
<220> FEATURE:
<223> OTHER INFORMATION: Description of Artificial Sequence:/note = Synthetic Construct

<400> SEQUENCE: 1
cgtctggatc cctcgagagc agcaccaagg tggacaagaa a          41

<210> SEQ ID NO 2
<211> LENGTH: 35
<212> TYPE: DNA
<213> ORGANISM: Artificial Sequence
<220> FEATURE:
<223> OTHER INFORMATION: Description of Artificial Sequence:/note = Synthetic Construct

<400> SEQUENCE: 2
gtgagaggac catttactag ggtccctagg cctct          35

<210> SEQ ID NO 3
<211> LENGTH: 35
<212> TYPE: DNA
<213> ORGANISM: Artificial Sequence
<220> FEATURE:
<223> OTHER INFORMATION: Description of Artificial Sequence:/note = Synthetic Construct

<400> SEQUENCE: 3
ttaaggtcga cagaggacca gggattggca ctgtg          35

<210> SEQ ID NO 4
<211> LENGTH: 35
<212> TYPE: DNA
<213> ORGANISM: Artificial Sequence
<220> FEATURE:
<223> OTHER INFORMATION: Description of Artificial Sequence:/note = Synthetic Construct

<400> SEQUENCE: 4
tctctcttcc tctagtgccg aaggcagctg cgata          35

<210> SEQ ID NO 5
<211> LENGTH: 35
<212> TYPE: DNA
<213> ORGANISM: Artificial Sequence
<220> FEATURE:
<223> OTHER INFORMATION: Description of Artificial Sequence:/note =
      Synthetic Construct

<400> SEQUENCE: 5
cgacctgacg gacgtttacg gaggcagctg cgata                          35

<210> SEQ ID NO 6
<211> LENGTH: 35
<212> TYPE: DNA
<213> ORGANISM: Artificial Sequence
<220> FEATURE:
<223> OTHER INFORMATION: Description of Artificial Sequence:/note =
      Synthetic Construct

<400> SEQUENCE: 6
ttaaggtcga cacggtggtc ggaggggatg tggag                          35

<210> SEQ ID NO 7
<211> LENGTH: 38
<212> TYPE: DNA
<213> ORGANISM: Artificial Sequence
<220> FEATURE:
<223> OTHER INFORMATION: Description of Artificial Sequence:/note =
      Synthetic Construct

<400> SEQUENCE: 7
cgacccctta tatatacatt ccagaggcag ctgcgata                       38

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence:/note =
      Synthetic Construct

<400> SEQUENCE: 8
ctcgagagca gcaccaaggt ggacaagaaa                                30

<210> SEQ ID NO 9
<211> LENGTH: 39
<212> TYPE: DNA
<213> ORGANISM: Artificial Sequence
<220> FEATURE:
<223> OTHER INFORMATION: Description of Artificial Sequence:/note =
      Synthetic Construct

<400> SEQUENCE: 9
gttctggccc tcgagagcag caccaaggtg gacaagaaa                      39

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence:/note =
      Synthetic Construct

<400> SEQUENCE: 10

Leu Glu Ser Ser Thr Lys Val Asp Lys Lys
1               5                   10

```
<210> SEQ ID NO 11
<211> LENGTH: 13
<212> TYPE: PRT
<213> ORGANISM: Artificial Sequence
<220> FEATURE:
<223> OTHER INFORMATION: Description of Artificial  Sequence:/note =
      Synthetic Construct

<400> SEQUENCE: 11

Val Leu Ala Leu Glu Ser Ser Thr Lys Val A sp Lys Lys
 1               5                  10
```

What is claimed is:

1. A fusion protein, comprising (A) an IgG sequence, (B) a nonantibody sequence covalently joined to the aminoterminal end of said IgG sequence and (C) a heterologous signal peptide that is covalently joined to the aminoterminal of said nonantibody sequence, wherein
   (i) said IgG sequence consists of a hinge region, a CH2 domain and a CH3 domain, in that order, said IgG sequence lacking a CH1 domain,
   (ii) said nonantibody sequence comprises an effector domain of a molecule selected from the group consisting of PDGF B, KGF, KGFR and β PDGFR,
   (iii) said heterologous signal peptide is a signal peptide of PDGF A.

2. The fusion protein according to claim 1, wherein said molecule is PDGF B.

3. The fusion protein according to claim 1, wherein said molecule is KGF.

4. The fusion protein according to claim 1, wherein said molecule is KGFR.

5. A fusion protein according to claim 1, where said molecule is β PDGFR.

* * * * *